(12) United States Patent
Figuly

(10) Patent No.: US 8,865,221 B2
(45) Date of Patent: Oct. 21, 2014

(54) SWELLABLE AND DEGRADABLE MICROSPHERES

(75) Inventor: Garret D. Figuly, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 642 days.

(21) Appl. No.: 12/984,693

(22) Filed: Jan. 5, 2011

(65) Prior Publication Data

US 2011/0097299 A1    Apr. 28, 2011

Related U.S. Application Data

(62) Division of application No. 12/221,560, filed on Aug. 4, 2008, now Pat. No. 7,887,846.

(60) Provisional application No. 60/963,718, filed on Aug. 7, 2007.

(51) Int. Cl.
*A61K 9/16* (2006.01)
*A61K 31/74* (2006.01)
*A61K 9/00* (2006.01)

(52) U.S. Cl.
CPC ............... *A61K 9/0019* (2013.01); *A61K 31/74* (2013.01); *A61K 9/1694* (2013.01); *A61K 9/1676* (2013.01); *A61K 9/1635* (2013.01)
USPC ..................................................... 424/497

(58) Field of Classification Search
CPC . A61K 9/5026; A61K 9/1694; A61K 9/1676; A61K 9/0019; A61K 9/1635; A61K 31/74
See application file for complete search history.

(56) References Cited

U.S. PATENT DOCUMENTS

| | | | |
|---|---|---|---|
| 4,446,261 A | 5/1984 | Yamasaki et al. | |
| 6,218,440 B1 | 4/2001 | Kitagawa | |
| 6,436,424 B1 | 8/2002 | Vogel et al. | |
| 6,511,744 B2 | 1/2003 | Centner et al. | |
| 6,590,094 B2 | 7/2003 | Karlou-Eyrisch et al. | |
| 6,713,646 B2 | 3/2004 | Zhang et al. | |
| 6,884,905 B2 | 4/2005 | Zhang et al. | |
| 7,135,593 B2 | 11/2006 | Zhang et al. | |
| 2001/0036451 A1 | 11/2001 | Goupil et al. | |
| 2003/0023021 A1 | 1/2003 | Sakuma | |
| 2003/0215519 A1 | 11/2003 | Schwarz et al. | |
| 2004/0161438 A1* | 8/2004 | Jungmann et al. | 424/401 |
| 2006/0251582 A1 | 11/2006 | Reb | |
| 2007/0237742 A1 | 10/2007 | Figuly et al. | |
| 2007/0237956 A1 | 10/2007 | Figuly et al. | |

FOREIGN PATENT DOCUMENTS

| | | |
|---|---|---|
| JP | 1994056676 A | 3/1994 |
| WO | WO0170289 A2 | 9/2001 |
| WO | WO03/094930 A1 | 11/2003 |

OTHER PUBLICATIONS

International Search Report Dated Jul. 7, 2009, International Application No. PCT/US2008/072261, International Filing Date Aug. 6, 2008.
Ficek et al, Novel preparation of poly (vinyl alcohol) microparticles without crosslinking agent for controlled drug delivery of proteins, Journal of Controlled Release, 1993, 259-264, vol. 27.
Thanoo et al, Barium sulphate-loaded p(HEMA) microspheres as artificial emboli: preparation and properties, Biomaterials, Sep. 1990, 477-481, vol. 11.

* cited by examiner

*Primary Examiner* — Sue Liu
*Assistant Examiner* — Jessica Kassa
(74) *Attorney, Agent, or Firm* — Kevin S. Dobson

(57) ABSTRACT

Swellable and degradable microspheres are described. The microspheres are prepared by a process that is reliable and high yielding, and makes use of a low temperature azo initiator, a small molecule chlorinated solvent as the organic phase, and a heat treatment step, and is carried out in absence of a crosslinking agent. The microsphere preparation made using the process is particularly useful as a degradable embolic material.

19 Claims, No Drawings

SWELLABLE AND DEGRADABLE MICROSPHERES

CROSS-REFERENCE TO RELATED APPLICATIONS

This application is a divisional of U.S. patent application Ser. No. 12/221,560, filed Aug. 4, 2008, which claims priority under 35 U.S.C. §119 from U.S. Provisional Application Ser. No. 60/963,718, filed Aug. 7, 2007.

FIELD OF INVENTION

The present invention relates to swellable and degradable hydrogel microspheres, including a process for preparing the hydrogel microspheres and a preparation of the swellable and degradable hydrogel microspheres.

BACKGROUND OF THE INVENTION

There is a need for swellable and degradable microspheres for use as a degradable embolic material for embolization treatment. Embolization involves the introduction of a material into the vasculature in order to block the blood flow in a particular region. This procedure may be used to treat non-cancerous tumors, such as uterine fibroids, as well as cancerous tumors. Vascular occlusion in the case of tumors may be used to suppress pain, limit blood loss during surgery, or to cause tumor necrosis. In addition, embolization treatment may be used to control bleeding caused by conditions such as stomach ulcers, aneurysms, and injury.

Non-degradable hydrogel microspheres have been produced and used in tissue augmentation and embolization treatments (see for example, U.S. Pat. No. 6,218,440, U.S. Pat. No. 4,446,261, U.S. Pat. No. 6,436,424, JP1994056676A, and copending and commonly owned US Patent Application Publication Nos. 2007/0237956 and 2007/0237742). However, degradable embolic microspheres would enable the administration of a number of different therapies (e.g., drug delivery and surgery) to a site without permanently occluding the site from blood flow. This could lead to more effective therapies and better patient response to treatments.

Degradable hydrogel microspheres are known in the art. One type of degradable microsphere incorporates degradable crosslinks. As the crosslinks degrade, the microsphere breaks down into soluble polymer chains (see for example U.S. Pat. No. 6,713,646, U.S. Pat. No. 6,884,905, and WO 2003/094930). Another type of degradable microsphere is prepared from degradable polymers such as poly(lactide-co-glycolide) copolymers. The disadvantage of both types of microspheres is that they may degrade into small insoluble fragments, which could lead to detrimental health effects.

Consequently, there is a need for swellable and degradable microspheres for use in therapy, which do not degrade into small fragments. The present invention satisfies this need and provides a new process for preparing swellable and degradable microspheres.

SUMMARY OF THE INVENTION

An embodiment of the invention provides a swellable and degradable microsphere preparation comprising microspheres which comprise polymer chains, said polymer chains comprising at least one monomer selected from the group consisting of acrylic acid, methacrylic acid, salts of acrylic acid and methacrylic acid, acrylamide, methacrylamide, N-substituted acrylamides, N-substituted methacrylamides, 2-hydroxyethyl acrylate, and 2-hydroxyethyl methacrylate,
provided that:
  if said monomer is acrylamide, methacrylamide, N-substituted acrylamides, 2-hydroxyethyl acrylate, or 2-hydroxyethyl methacrylate, then said monomer is present in combination with at least one other monomer selected from subgroup 1 consisting of: acrylic acid, methacrylic acid, and salts of acrylic acid and methacrylic acid;
wherein:
  (i) said polymer chains are not crosslinked with a crosslinking agent; and
  (ii) said microspheres degrade substantially completely into high molecular weight soluble polymer after a time greater than 20 minutes in vitro when incubated in phosphate-buffered saline solution in a shaker oven set at 37° C. and 20 revolutions per minute.

In another embodiment, the microsphere preparation is made by a process comprising the steps of:
  a) forming a first solution having a pH of at least 3 or about 3 comprising:
    (i) water;
    (ii) at least one water miscible monomer selected from the group consisting of acrylic acid, methacrylic acid, salts of acrylic acid and methacrylic acid, acrylamide, methacrylamide, N-substituted acrylamides, N-substituted methacrylamides, 2-hydroxyethyl acrylate, and 2-hydroxyethyl methacrylate,
      provided that:
        (A) if said monomer is acrylamide, methacrylamide, N-substituted acrylamides, 2-hydroxyethyl acrylate, or 2-hydroxyethyl methacrylate, said monomer is used in combination with at least one other monomer selected from subgroup 1 consisting of: acrylic acid, methacrylic acid, and salts of acrylic acid and methacrylic acid;
    (iii) a water soluble protecting colloid;
    (iv) an emulsifier; and
    (v) a water soluble azo initiator having a low activation temperature;
  b) forming a second solution comprising at least one substantially chlorinated hydrocarbon of less than 6 carbon units,
    provided that the chlorinated hydrocarbon is not a halogenated aromatic hydrocarbon, and an organic soluble protecting colloid;
  c) forming a first suspension with agitation comprising the first and second solutions at a temperature below the activation temperature of the azo initiator of (a);
  d) increasing the temperature of the first suspension to a temperature at which the water soluble azo initiator is activated;
  e) agitating the first suspension until it forms a second suspension comprising a gelatinous precipitate suspended in an organic liquid phase, wherein microspheres are formed;
  f) allowing the second suspension to cool to a temperature that is at about 30° C. or below 30° C. while agitating the second suspension;
  g) washing the second suspension at least once with a dehydrating solvent wherein water is removed from the microspheres, producing a microsphere slurry comprising washed microspheres;
  h) recovering the washed microspheres from the microsphere slurry; and i) heating the washed microspheres to a temperature above 25° C. for a time sufficient to substantially dry the washed microspheres to form the swellable and degradable microsphere preparation;

wherein the process is carried out in absence of a crosslinking agent.

Another embodiment provides a method for embolization in a mammal comprising administering into the vasculature of the mammal, the swellable and degradable microsphere preparation disclosed herein.

DETAILED DESCRIPTION

In one embodiment, the present invention provides a process for preparing swellable and degradable microspheres which is simple, consistent, and produces microspheres with valuable properties at a high yield. The process makes use of a water soluble, low temperature-active azo initiator in an aqueous solution of monomer and emulsifier. A chlorinated organic medium is used in forming a suspension with the aqueous solution. The aqueous solution and organic medium both additionally include protecting colloids. The aqueous solution and organic medium, as well as the mixture of the two, are initially held below the activation temperature of the azo initiator. The organic medium, which may comprise a chloroform and methylene chloride mixture, should have a high enough boiling temperature that the water soluble azo initiator can be activated to cause polymerization producing microspheres. The resulting microspheres are washed with a dehydrating solvent and then dried at a temperature of above 25° C. The process is carried out in absence of a crosslinking agent. It has been unexpectedly discovered that the omission of a crosslinking agent from the process of forming the microspheres and heat treating the resulting microspheres provides swellable and degradable microspheres that fully swell and remain dimensionally stable for at least several days.

In another embodiment, the invention provides a preparation of swellable and degradable microspheres that is produced according to the process disclosed herein. The swellable and degradable microspheres are useful as a degradable embolic material, which may allow the administration of a number of different therapies to a site without permanently occluding the site from blood flow.

When an amount, concentration, or other value or parameter is recited herein as either a range, preferred range or a list of upper preferable values and lower preferable values, the recited amount, concentration, or other value or parameter is intended to include all ranges formed from any pair of any upper range limit or preferred value and any lower range limit or preferred value, regardless of whether such ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The following definitions and abbreviations are to be used for the interpretation of the claims and the specification.

The term "microspheres" or "microsphere" refers to either a population of micron size particles, or an individual particle, depending upon the context in which the word is used, which has a high sphericity measurement. The sphericity measurement of a population of microspheres may be in the range of about 80% to about 100%, with 95% being typical. The microspheres are substantially spherical, although a microsphere population may include some individual particles that have a lower sphericity measurement.

The term "miscible" refers to the ability of two liquids to mix without separating into two separate phases. In addition, a solid is miscible if a solution made with the solid is miscible with another liquid. Specifically, a liquid monomer may itself be miscible with water. A solid monomer is water miscible when an aqueous solution prepared with the solid monomer can be mixed with water without having the mixture separate into two separate phases.

The term "substantially chlorinated hydrocarbon" refers to a hydrocarbon that is from 50% to fully chlorinated. Carbon tetrachloride is an example of such a hydrocarbon.

The term "slurry" refers to a composition that comprises a particulate material in a liquid.

The terms "first suspension" and "second suspension" refer to suspensions formed during the process of preparing microspheres that is described herein.

The term "embolization suspension" refers to a suspension that contains microspheres and is administered using a catheter and/or needle for embolization treatment.

The term "deformable" refers to the property of being able to change shape in response to an external pressure. Microspheres are deformable if they do not retain their shape when they are swelled, following uptake of an aqueous medium, and are subjected to pressure.

The term "degradable" refers to the property of the microspheres disclosed herein whereby the microspheres break down substantially completely into high molecular weight soluble polymer within a period of about 30 days in vitro when incubated in phosphate-buffered saline solution in a shaker oven set at 37° C. and 20 revolutions per minute (rpm), as described in Examples 3 and 4 below. The high molecular weight soluble polymer resulting from the degradation of the microspheres has a molecular weight distribution, determined by size exclusion chromatography as described in General Methods herein below, characterized by a weight-average molecular weight ($M_w$) of about 500,000 to about 1,200,000 Daltons, and a number-average molecular weight ($M_n$) of about 150,000 to about 975,000 Daltons.

Monomers

Monomers that can be used in the present process for preparing swellable and degradable microspheres include acrylic acid and salts (such as sodium and ammonium) of acrylic acid. Other monomers that may be suitable are water miscible monomers including, but not limited to, methacrylic acid, salts (such as sodium and ammonium) of methacrylic acid, acrylamide, methacrylamide, N-substituted acrylamides, N-substituted methacrylamides, 2-hydroxyethyl acrylate, and 2-hydroxyethyl methacrylate. Monomers may be used singly or in combinations as co-monomers. Monomers that may be used as single monomer components (subgroup 1) include acrylic acid, methacrylic acid, and salts (such as sodium and ammonium) of acrylic acid and methacrylic acid. Preferably, the following monomers are used as co-monomers with at least one of the monomers from subgroup 1: acrylamide, methacrylamide, N-substituted acrylamides, N-substituted methacrylamides, 2-hydroxyethyl acrylate, and 2-hydroxyethyl methacrylate. Most useful in producing microspheres for medical applications are monomers having biocompatibility such as acrylic acid, methacrylic acid, salts of acrylic acid and methacrylic acid, 2-hydroxyethyl acrylate and 2-hydroxyethyl methacrylate, and combinations thereof. In one embodiment the monomer is a combination comprising acrylic acid and sodium acrylate.

Many of these monomers are liquids which are miscible with water. For monomers that are solids, an aqueous solution of the monomer may be prepared, and this monomer solution is miscible with water. Acid monomers and salts of monomers may be combined to adjust the pH of a monomer solution. It is particularly useful to partially neutralize an acid monomer, thereby providing a mixture of acid monomer and monomer salt. Acid monomers that may be used are, for example, acrylic acid, methacrylic acid and combinations thereof. A monomer prior to partial neutralization is referred to as an initial monomer. An acid monomer is typically partially neutralized using a base. Suitable bases include, but are not limited to, sodium hydroxide, potassium hydroxide, ammonium hydroxide, lithium hydroxide and combinations thereof. Bases containing divalent cations, such as calcium hydroxide and barium hydroxide may also be used; however, they are preferably used in combination with a base containing monovalent cations because divalent cations have a strong tendency to induce ionic crosslinking, which could severely alter the desirable properties of the microspheres. For some applications it may be desirable to substitute a portion of the base with barium hydroxide $(Ba(OH)_2)$ to introduce a radio-opaque element, which makes the resulting microspheres amenable to x-ray imaging. Barium hydroxide may be used in a ratio of up to about 1:1 by weight of $Ba(OH)_2$ to NaOH, to produce a combination salt that includes barium salt. Alternatively, a barium monomer salt may be included in a monomer combination.

First Solution

A monomer, as described above, is prepared in an aqueous solution, together with additional components, which is herein called the "first solution". The first solution does not comprise a crosslinking agent, which is used in methods known in the art. The monomer is generally included at about 0.5% to about 30% as weight percent of the first solution. Monomer weight percents of about 15% to about 25% and about 20% to about 25% are particularly useful in the process of the invention. If a combination of monomers is used in the process, the total amount of all the monomers is about 0.5% to about 30%, in addition from about 15% to about 25%, and in addition from about 20% to about 25%, as weight percent of the first solution.

The pH of the first solution may vary and is a factor in the swell capacity of the microspheres prepared in the process of the invention. The useful pH range of the first solution is at least about 3, preferably between about 3.5 and about 10, more preferably between about 5 and about 9, to produce microspheres with a high swell capacity.

The pH of the first solution may be adjusted in any number of ways. For example, if the monomer is prepared as a monomer solution, as described above, the pH of the monomer solution will govern the pH of the first solution. In the case of an acid monomer, the pH of the monomer solution is related to the amount of base or monomer salt added to the acidic monomer solution. Alternatively, the pH of the first solution may be adjusted as required by the addition of acid or base after all the components have been added.

Included in the "first solution" is a component that can modify the viscosity of an aqueous solution to provide a surface tension that allows droplet formation in the aqueous/organic suspension that is formed during the present microsphere preparation process. This component is referred to herein as a "protecting colloid". A variety of natural and synthetic compounds that are soluble in aqueous media may be used as a protecting colloid including cellulose derivatives, polyacrylates (such as polyacrylic acid and polymethacrylic acid), polyalkylene glycols such as polyethylene glycol, partially hydrolyzed polyvinyl alcohol and other polyols, guar gum, and agar gum. Particularly useful are cellulose ethers such as methyl cellulose, hydroxymethyl cellulose, hydroxyethyl cellulose, ethylhydroxyethyl cellulose, hydroxypropyl cellulose, ethyl cellulose, and benzyl cellulose; as well as cellulose esters such as cellulose acetate, cellulose butylate, cellulose acetate butylate, cellulose propionate, cellulose butyrate, cellulose acetate propionate, cellulose acetate butyrate, and cellulose acetate phthalate. The amount of the protecting colloid in the first solution is sufficient to reduce microdroplet coalescence in the aqueous/organic suspension, and is generally between about 0.1% and about 3% by weight of the first solution. Preferred is methyl cellulose at about 0.5% to about 0.6% by weight.

An emulsifier is included in the first solution to promote the formation of a stable emulsion on addition of the first solution to an organic second solution (described below). Any emulsifier which stabilizes the aqueous/organic emulsion may be used. Suitable emulsifiers include, but are not limited to, alkylaryl polyether alcohols such as the Triton™ X nonionic surfactants commercially available from Union Carbide (Danbury, Conn.). These products generally contain mixtures of polyoxyethylene chain lengths and include, for example, Triton® X-100: polyoxyethylene(10) isooctylphenyl ether; Triton® X-100, reduced: polyoxyethylene(10) isooctylcyclohexyl ether; Triton® N-101, reduced: polyoxyethylene branched nonylcyclohexyl ether; Triton® X-114: (1,1,3,3-tetramethylbutyl)phenyl-polyethylene glycol; Triton® X-114, reduced: polyoxyethylene(8) isooctylcyclohexyl ether; Triton® X-405, reduced: polyoxyethylene(40) isooctylcyclohexyl ether; and Triton™ X-405: polyoxyethylene (40) isooctylphenyl ether, 70% solution in water. Particularly suitable is Triton™ X-405, 70 wt % solution, which is an alkylaryl polyether alcohol preparation having an average of at least about 30 ethylene oxide units per ether side chain. Typically, the emulsifier in the first solution is used at a concentration of about 1% to about 10% by weight of the first solution.

In addition, the first solution includes a polymerization initiator. The initiator used in the process of the invention is a water soluble azo initiator which has a low activation temperature. Azo initiators are substituted diazo compounds that thermally decompose to generate free radicals and nitrogen gas. The temperature of activation of the azo initiator used is low enough so that the boiling point of an organic second solution (described below) is above the azo initiator activation temperature. Examples of suitable low temperature water soluble azo initiators include, but are not limited to, 2,2'-azobis(2-amidinopropane)dihydrochloride; 4,4'-azobis(4-cyanopentanoic acid); and 2,2'-azobis(2-[2-imidazolin-2-yl]) propane dihydrochloride. A particular azo initiator, having a particular activation temperature, is used with an organic second solution composition (described below) at a temperature and with a reaction time period that is effective in initiating polymerization. Most effective is use of an azo initiator at a temperature that is close to its optimal activation temperature and which is also below the boiling temperature of the organic second solution. However, an azo initiator may be used at a temperature that is lower than its optimal activation temperature in order to stay below the boiling temperature of the organic second solution, but this will require a longer reaction time for polymerization. A particularly suitable azo initiator has an activation temperature that is less than about 55° C. and this azo initiator is used with an organic second solution having a boiling temperature of about 55° C. A particularly suitable azo initiator is VA-044™ (2,2'-azobis(2-[2-imidazolin-2-yl])propane dihydrochloride, commercially available from Wako Pure Chemical Industries, Ltd., Richmond, Va.) having an activation temperature of between 51° C. and 52° C.

The azo initiator has advantages over other initiators such as persulfates and hydroperoxides. The azo initiator is effective when used in very low amounts, in contrast to other initiators. The azo initiator is used at about 0.1% to 1.0% by weight of monomer. Preferably about 0.5% azo initiator is used. The low level of azo initiator results in very low levels of initiator contamination in the polymerized hydrogel as compared to contamination resulting from use of other initiators. In addition, there is no metal contamination resulting from the azo initiator, while other initiators typically include metal catalysts that do leave metal contamination in the polymerized product. In addition, other typical initiators are sensitive to oxygen, and, therefore, solutions in contact with these initiators must be de-aerated. The remaining oxygen content of the de-aerated solutions is variable, leading to inconsistency in the microsphere forming process. With use of an azo initiator, no de-aeration is required, which reduces the complexity of solution preparation for use in the microsphere formation process and increases the consistency of microsphere preparation. In addition persulfate initiators generally give more inconsistent conversion and yields of microspheres than azo initiators.

Second Solution

An organic solution acts as a dispersion medium in the process of microsphere preparation, and is herein called the "second solution". The second solution comprises at least one substantially chlorinated hydrocarbon of less than 6 carbon units, excluding halogenated aromatic hydrocarbons. A substantially chlorinated hydrocarbon may be a hydrocarbon that is at least 50% chlorinated, as well as a fully chlorinated hydrocarbon. Particularly suitable is a chlorinated solvent that readily dissolves ethyl cellulose to a homogeneous solution, boils above at least about 50° C. and has a density able to support microsphere formation in aqueous/organic suspension. A particularly useful organic medium in the process of microsphere preparation is a mixture containing chloroform and methylene chloride. Methylene chloride alone does not have a high enough boiling temperature to allow the use of a low temperature aqueous azo initiator. Chloroform alone is not sufficient to support microsphere formation. The combination of chloroform and methylene chloride provides an organic solution which has a boiling temperature allowing use of a low temperature aqueous azo initiator and which supports microsphere formation in the aqueous/organic suspension. Chloroform and methylene chloride may be used in volume ratios between about 20:1 and about 1:20. More suitable is a chloroform and methylene chloride solution with a volume ratio between about 5:1 and 1:5. Particularly suitable is a volume ratio of 3:1 chloroform:methylene chloride solution which has a boiling temperature of about 53° C.

Additionally, other solvents or solvent mixtures may be used in combination with a substantially chlorinated hydrocarbon such as methylene chloride. For example, it may be desirable to substitute for chloroform in the chloroform-methylene chloride mixtures described above because of the health hazards of chloroform. Suitable solvent or solvent mixtures to substitute for chloroform may be selected by matching the Hansen solubility parameters (Hansen, *Hansen Solubility Parameters, A User's Handbook*, CRC Press LLC, Boca Raton, Fla., 2000) of particular solvent or solvent mixtures to those of chloroform. The Hansen solubility parameters are an extension of the Hildebrand solubility parameters. According to Hansen, "the basis for the Hansen Solubility Parameters (HSP) is that the total energy of vaporization of a liquid consists of several individual parts, that arise from (atomic) dispersion forces, (molecular) permanent dipole-permanent dipole forces and (molecular) hydrogen bonding (electron exchange)." Materials having similar HSP have high affinity for each other. The basic equation for the HSP is that the total cohesion energy, E, must be the sum of the individual energies:

$$E = E_D + E_P + E_H$$

Where $E_D$ is the Hansen dispersion cohesion energy, $E_p$ is the Hansen polarity cohesion energy, and $E_H$ is the Hansen hydrogen bonding cohesion energy. Dividing this expression by the molar volume, gives the total Hildebrand solubility parameter as the sum of the squares of the Hansen components:

$$\delta^2 = \delta_D^2 + \delta_P^2 + \delta_H^2$$

Chloroform has a Hansen dispersion of 17.8, Hansen polarity of 3.1 and Hansen hydrogen bonding of 5.7 in units of the square root of megapascals ($mPa^{1/2}$). A software program (Molecular Modeling Pro Plus, ChemSW, Fairfield, Calif.) is available to calculate the Hansen solubility parameters from molecular structure. Preferred solvent mixtures have a sum of the differences (in absolute value) in Hansen solubility parameters relative to the Hansen solubility parameters of chloroform of less than about 0.21. A sample calculation of the sum of the differences in Hansen solubility parameters for a mixture of 30 vol % (percent by volume) ethyl heptanoate and 70 vol % phenethyl acetate relative to chloroform is shown in Table A. Suitable solvent mixtures are given in Table B.

TABLE A

Calculation of the Sum of the Differences in Hansen Solubility Parameters for a Mixture of 30 vol % Ethyl Heptanoate and 70 vol % Phenethyl Acetate relative to chloroform

| Hansen Parameter | [1] Chloroform | [2] Ethyl Heptanoate | [3] Penethyl Acetate | 0.3 × [2] + 0.7 × [3] | Difference |
|---|---|---|---|---|---|
| Dispersion | 17.8 | 16.254 | 18.520 | 17.840 | 0.040 |
| Polarity | 3.1 | 3.025 | 3.123 | 3.093 | 0.007 |
| Hydrogen Bonding | 5.7 | 4.686 | 6.034 | 5.630 | 0.070 |

Sum of differences = 0.117

TABLE B

Solvent Mixtures that Can be Substituted for Chloroform

| Solvent Mixture (% by volume) | Difference in Hansen Solubility Parameters Relative to Chloroform |
|---|---|
| 20% methyl oleate:80% phenethyl acetate | 0.1180 |
| 30% ethyl heptanoate:70% phenethyl acetate | 0.1170 |
| 30% methyl octanoate:70% phenethyl acetate | 0.1352 |
| 40% diethyl carbonate:60% methylphenyl acetate | 0.1457 |
| 20% phenylpropyl methyl ether:80% phenyl propyl ether | 0.1501 |
| 70% ethyl phenyl ether:30% phenylpropyl acetate | 0.1570 |
| 20% diethylene glycol butyl ether:80% phenylpropyl methyl ether | 0.1703 |
| 20% ethyl propionate:80% phenylpropyl acetate | 0.1740 |
| 80% phenylpropyl acetate:20% tripropylamine | 0.1856 |
| 90% phenyl propyl ether:10% toluene | 0.2015 |
| 30% methyl hexanoate:70% phenylpropyl acetate | 0.2048 |
| 20% isopropyl palmitate:80% phenethyl acetate | 0.2073 |

In one embodiment, the second solution comprises a combination of a solvent mixture of 30 vol % ethyl heptanoate (CAS No. 106-30-9) and 70 vol % phenethyl acetate (CAS No. 103-45-7), with methylene chloride in a volume ratio of about 20:1 to about 1:20, in addition about 5:1 to about 1:5, and further in addition of about 3:1.

The second solution also comprises a viscosity modifying component that provides a surface tension that allows droplet formation in the aqueous/organic suspension formed during the present microsphere preparation process. This viscosity modifying component is again called a "protecting colloid". A variety of natural and synthetic compounds soluble in organic media may be used as a protecting colloid, including, but not limited to, cellulose derivatives, polyacrylates (such as polyacrylic acid and polymethacrylic acid), polyalkylene glycols such as polyethylene glycol, partially hydrolyzed polyvinyl alcohol and other polyols, guar gum, and agar gum. Particularly useful are organic soluble cellulose ethers such as methyl cellulose, hydroxymethyl cellulose, hydroxyethyl cellulose, ethylhydroxyethyl cellulose, hydroxypropyl cellulose, ethyl cellulose, and benzyl cellulose; as well as organic soluble cellulose esters such as cellulose acetate, cellulose butylate, cellulose acetate butylate, cellulose propionate, cellulose butyrate, cellulose acetate propionate, cellulose acetate butyrate, and cellulose acetate phthalate. The amount of the protecting colloid in the organic second solution is sufficient to reduce microdroplet coalescence in the aqueous/organic suspension, and is generally between about 0.5% and about 5% by weight of the organic second solution. Particularly suitable is ethyl cellulose at about 1.5% by weight.

Process for Making a Swellable and Degradable Microsphere Preparation

The process for the preparation of the swellable and degradable microspheres disclosed herein is carried out in absence of a crosslinking agent. The first solution and the second solution are combined with agitation to form a first suspension. The second solution is used in an amount that is adequate to form a good suspension, while the amount may be as great as is practical. Generally the volume ratio of second to first solutions is in the range of about 10:1 to about 2:1. Preferably the volume ratio of second to first solutions is in the range of about 6:1 to about 4:1.

The first and second solutions may be combined in any order. Specifically, the first solution can be added to the second solution, the second solution can be added to the first solution, or the two solutions can be combined simultaneously. Preferably, the first solution is added to the second solution. During the combination of the first and second solutions, the resulting mixture is agitated at a rate capable of forming a uniform suspension from the two solutions. Agitation may be by any method which thoroughly mixes the two solutions, such as shaking or stirring. Typically, the second solution is stirred in a container while the first solution is poured into the same container. The combined first and second solution is agitated at a temperature that is below the azo activation temperature (and above the freezing point of the solution) to form a uniform, first suspension. Generally the temperature is below about 50° C., and more typically is below about 40° C. A temperature that is below about 30° C. is preferred. Typically the first suspension is stirred at about 100 to 600 rpm, depending on the size of the container, at room temperature for about one-half to one hour.

The agitation of the first suspension allows formation of small droplets in the suspension. The size of the forming droplets, and therefore the size of the microspheres that are produced, is related to the rate of agitation. As the agitation is reduced, droplets coalesce. Agitation is maintained at a rate sufficient to reduce droplet coalescence allowing the formation of micron sized microspheres. For example, for the formation of microspheres in the size range of 40 to 500 microns, stirring is typically about 150-250 rpm when using a one liter container. The optimum agitation rate for any particular system will depend on many factors, including the particular monomer, and solvent system used, the geometry of the container, the geometry of the agitator, and the desired microsphere properties for the intended application. In general, larger microspheres are obtained at lower agitation rates. The agitation rate for any given conditions can be readily optimized by one skilled in the art using routine experimentation.

After the formation of the first suspension, a low level of heat is applied such that the temperature of the first suspension is brought to a temperature that is below the boiling temperature of the first solution, and below or at the boiling temperature of the second solution. Typically the temperature is between about 50° C. and 55° C., depending on the mixture of the second solution. It is preferred to bring the temperature of the first suspension made with a chloroform and methylene chloride ratio of about 3:1 to about 51° C. to 52° C. At this temperature the low temperature azo initiator is activated. The first suspension is agitated until it forms a second suspension comprising a precipitate of gelatinous microspheres in the suspending medium, which is predominantly an organic liquid phase. The gelatinous precipitate appears as a milky material which falls out of the suspension. Additionally, a white foam may be seen on top of the second suspension. Typically stirring of the first suspension to form the second suspension at the elevated temperature is for about 8-10 hours. The second suspension is agitated for another period of time at room temperature to ensure that the polymerization and microsphere formation are complete. During this time the second suspension cools to a temperature which is easily handled. Generally this is at or below about 30° C. Room temperature, typically between about 20° C. to about 25° C., is conveniently used. Typically stirring remains at about 150-250 rpm, when using a one liter container, for about 8-14 hours.

Agitation is ceased, allowing the formed microspheres to settle to the bottom of the container. Removing the water from these hydrogel microspheres may be accomplished by washing with a dehydrating solvent such as methanol, ethanol, or acetone. Particularly useful is methanol, which is added, and the mixture is optionally agitated gently for about an hour to allow good solvent exchange. The microspheres are then recovered by a method such as decanting or filtering, and may be washed a second time with methanol and again recovered. With removal of the water, the microspheres change in appearance from milky and gelatinous to hard and opaque white. The microspheres finally may be washed in ethanol, which is desirable for removal of residual methanol, particularly for microsphere use in medical applications. The washed microspheres in the dehydrating solvent form a microsphere slurry comprising washed microspheres. The washed microspheres may be recovered from the microsphere slurry by a method such as decanting or filtering.

The washed microspheres are heated to dry the microspheres, forming a powder of microspheres. Heating rids the microspheres of remaining washing solvent and additional water. While not wishing to be bound by any particular theory, it is believed that heating may also aid in the formation of crystalline domains in the microspheres, which behave as "pseudo-crosslinks" that provide dimensional stability. Heating is done at a temperature above 25° C., preferably at least about 50° C., more preferably about 50° C. to about 150° C. for a time sufficient to substantially dry the microspheres to form the swellable and degradable microspheres disclosed herein. Typically, the heating time is at least about 24 h. As is known in the art, lower temperatures require longer drying times. Additionally, the degradation rate of the microspheres can be controlled by the heating temperature and time. Generally, lower temperatures and shorter heating times result in hydrogels with faster degradation rates, as shown in Examples 7-16 herein below. Additionally, the washed microspheres may be dried at room temperature (i.e., about 20° C. to about 25° C.) and then subjected to the heat treatment to form the swellable and degradable microspheres. The optimum heating conditions to produce a degradable microsphere preparation for any particular application can be readily determined by one skilled in the art using routine experimentation. In one embodiment, the heating is done at a temperature of about 100° C. for a period of 48 to 72 hours.

Substantially dry microspheres may contain a small amount of water after heating. The amount of remaining water may be about 1% to 10% of the microsphere total weight. The resulting microsphere preparation, though retaining a small amount of water in the microspheres, flows when tilted or swirled in a container and thus forms a free-flowing dry microsphere powder.

The microsphere preparation prepared by the method described herein comprises microspheres that are typically in the size range of about 10 to about 750 microns in diameter, in addition from about 14 to about 730 microns in diameter. A prevalence of the microspheres is in the size range of about 25 to about 250 microns in diameter, as seen when analyzing a small sample size of microspheres. A heterogeneous size mixture of microspheres may be separated into microsphere samples of specific size ranges, if desired, for specific applications. Microspheres may be separated by methods such as fluidized bed separation and sieving, also called screen filtering. Particularly useful is sieving through a series of sieves appropriate for recovering samples containing microspheres of desired sizes. For example, separate samples of microspheres may be obtained using a series of sieves with mesh sizes of 35 to 400 microns. Separate microsphere samples may be obtained that have diameters ranging between about 30 and about 44 microns; about 115 and about 165 microns; about 180 and about 330 microns; and with size ranges also falling between and outside of these exemplary groups. These samples of size separated microspheres exemplify the production of microsphere preparations having a predominant size ranging between about 30 microns and 600 microns in diameter and including microspheres in a size range that is generally within +/−30% of the median for about 90% of the sample. Microsphere preparations may be produced having microspheres in a size range that is generally within +/−20% of the median for about 90% of the sample.

Microsphere Properties Advantageous for Embolic Applications

Microspheres prepared by the present process are biocompatible in that they lack cytotoxicity, are non-inflammatory, and are non-hemolytic. The microspheres have a swell response in whole blood that is similar to the swell response in water, achieving up to 100-fold swell within seconds. Additionally, the microspheres degrade into high molecular weight soluble polymer after a period of time. Moreover, the resistance to fracture of the microspheres described herein makes them particularly suitable for embolization since resistance to fracture reduces the potential for effects such as embolism downstream of the target site, unwanted inflammatory response, exacerbation of clotting cascade, and loss of therapeutic occlusion. These properties make the microspheres ideally suited for use as a temporary embolic material.

The Swellable and Degradable Microsphere Preparation

The microsphere preparation of the present invention is prepared according to the process disclosed herein and contains swellable and degradable microspheres having the properties described herein. The microsphere preparation is a microsphere powder. The microsphere powder may be made available for use as a powder or for addition of a liquid appropriate to the intended use. Addition of a liquid to the microsphere powder produces a microsphere slurry or microsphere suspension. Liquids used in a microsphere suspension may be any that are appropriate for the intended use. For example, a biocompatible liquid that controls swell is used to suspend microspheres for embolization. Typical swell-control biocompatible liquids include, for example, propylene glycol, dimethylsulfoxide (DMSO), Ethiodol®, MD-76®, Omnipaque™, Visipaque™, and mineral oil. Ethiodol® MD-76®, Omnipaque™, and Visipaque™, are contrast agents typically used in medical intravascular arteriography or lymphography procedures. Ethiodol® contains iodine organically combined with ethyl esters of the fatty acids of poppyseed oil and is available from SAVAGE Laboratories® (Melville, N.Y.). MD-76® is an aqueous solution of diatrizoate meglumine (CAS No. 131-49-7, 66 wt %) and diatrizoate sodium (CAS No. 737-31-5, 10 wt %) buffered with monobasic sodium, with a pH of 6.5 to 7.7, having organically bound iodide to provide for radiological visualization. MD-76® is manufactured by Mallinckrodt Inc. (St. Louis, Mo.). Omnipaque™, and Visipaque™ (GE Healthcare, Inc., Princeton, N.J.) are aqueous solutions containing Iodixanol (CAS No. 92339-11-2).

Embolization Suspension

A swellable and degradable microsphere preparation made according to the present process is used to prepare a suspension for embolization treatment, herein called an "embolization suspension". Sterility is an important factor in embolization treatment. The described microsphere preparation process including a final ethanol wash, provides a sterilization treatment. Further sterilization may be performed by extending the ethanol wash for a long period of time, such as overnight. Sterility may be enhanced by using additional measures such as carrying out the process for making the microspheres in a sterile environment, and treating the microsphere preparation with UV light, ethylene oxide or gamma radiation, as is known to one skilled in the art.

The embolization suspension includes a biocompatible carrier. The carrier provides not only a medium to suspend and administer the microspheres, but also to control the swelling of the microspheres. Typically, the carrier used in the suspension has a low enough viscosity to allow delivery of the microspheres through small-bore needles and catheters, such as those of 20 gauge or 7 French (F) or smaller. A gauge measurement is used for needles, while a French measurement is used for catheters, both of which designate the outside diameter. The inside diameter of a needle or catheter is related to the outside diameter, but also depends on the thickness of the wall and so can vary between manufacturers. Thus precise measurements of the inside diameters of needles and catheters are not specified by the gauge or French unit. However, inside bore diameters of specific catheters and needles are known or can readily be obtained by one skilled in the art. Biocompatible carriers that limit swell of the microspheres, and thus are swell-control media, include the commonly used contrast agents Ethiodol® (SAVAGE Laboratories®, Melville, N.Y.), MD-76® (Mallinckrodt Inc., St. Louis, Mo.), and Omnipaque™ and Visipaque™ (both available from GE Healthcare, Inc.). In addition, swell may be controlled by salt concentration and ionic strength, as well as with pH or DMSO. Particularly suitable biocompatible carriers are those containing DMSO above about 60% concentration, those with an acidic pH, and contrast agents. The contrast agent MD-76® allows some swell, ranging between about 3.5× and about 7.5× the original volume, and may be used as a swell-control medium. Different carriers may be mixed, such as combining a percentage of DMSO and a contrast agent to establish the desired amount of microsphere swell (explained below) in the embolization suspension.

The microsphere concentration in the embolization suspension varies depending on the carrier used and the size catheter to be used for administering the suspension, which in turn depends on the size of the vasculature to be embolized. In addition, the size of the microspheres affects the concentration used, where samples of different sized microspheres may be prepared, for example by sieving, as described above. For example, 250 mg/mL concentration of approximately 250 micron microspheres in DMSO (no swell) may be used with catheters of 6 F and larger. For delivery of high concentrations of microspheres with smaller catheters, such as 5 F and smaller, it may be desirable to have limited swell of the microspheres for administering the microsphere suspension. The limited swell may take place prior to or during the administering. The limited swell may be up to about 10× the original volume of the microspheres. Limited swell provides deformability of the microspheres which allows them to pass through small diameter catheters and needles. Limited swell may be achieved by methods such as adjusting the salt concentration, pH or DMSO concentration of the carrier, or with use of a contrast agent. For example, with about 50% or less DMSO concentration in the carrier, the microspheres begin to swell. In addition, the microspheres may swell to between about 3.5× and 7.5× the original volume in contrast agent. The specific size and concentration of microspheres, as well as the desired carrier, may be chosen by one skilled in the art for the particular embolization treatment to be performed.

Embolization Treatment

The embolization suspension containing the swellable and degradable microsphere preparation made as described herein is administered to a mammal for embolization, as is known to one skilled in the art, for example as described in "Uterine Artery Embolization and Gynecologic Embolotherapy", Spies and Pelage, 2005 ISBN: 0-7817-4532-2 and in "Vascular and Interventional Radiology: Principles and Practice", Bakal et al., 2002 ISBN: 0-86577-678-4. Administration of the embolization suspension containing microspheres prepared by the present process is generally by passage through a catheter or needle into the vasculature of the mammal such that the microspheres reach a target site. As the embolization suspension contacts the blood in the vasculature, the microspheres swell and form an occlusion. The occlusion effectively blocks the blood flow distal to the occlusion site. The occlusion site may be any target site where, for medical treatment, it is desired to block the flow of blood. For example, the occlusion site may be in a blood vessel that feeds a tumor such as a uterine fibroid or a cancerous tumor, in an arteriovenous malformation, or in a blood vessel where the blood is not contained, such as in the case of a stomach ulcer or injury. Preoperative embolization may also be performed to stop blood flow to a region targeted for surgery.

Some typically used media, such as Ethiodol®, are too viscous to pass through microcatheters. Thus alternative media with low viscosity, yet the ability to limit microsphere swell, are used in embolization suspensions delivered with microcatheters. The small volume of microspheres, prepared by the present process that is delivered for forming an occlusion allows the use of suspension media that may cause ill effects when injected into a mammal in larger volumes. For example, media including more than 60% DMSO or media with a pH in the range of 2-3 may be used in embolization suspensions to control microsphere swelling. Several milliliters of these media may be administered to deliver an adequate amount of microspheres to form an occlusion. Additionally, for minimizing effects of potentially harmful media, a buffering solution may be administered prior to and after administering the embolization suspension. Phosphate buffered saline or bicarbonate buffer are examples of solutions that may be used in this manner.

In addition to forming an occlusion, the present microspheres used in embolization may also be prepared such that they are able to deliver medications, such as pharmaceutical drugs or therapeutic agents. The medication may be loaded into the microspheres using various methods known in the art. For example, the microspheres may be imbibed with the medication by swelling the microspheres in a medium containing the medication and allowing it to soak into the microspheres. The microspheres may then be dried or deswelled by removing water by washing with a dehydrating solvent, as described above. Additionally, the medication may be coated onto the microspheres using methods such as spraying, immersion, and the like. The medication may also be directly incorporated into the microspheres during their preparation by adding the medication to the first solution. Following delivery of the microspheres containing the medication to the target site, the pharmaceutical drug or therapeutic agent is released over time as the microspheres are in contact with body fluids. For example, anti-cancer drugs may be delivered by microspheres forming an occlusion in proximity to a cancerous tumor. Delivery in embolizing microspheres of agents such as anti-angiogenic factors, anti-inflammatory drugs, analgesics, and local anesthetics provide additional treatment to the physical blockage of embolization. Additional therapeutic agents that may be delivered in the present microspheres are described in WO 01/72281.

Kits

Further provided is a kit including swellable and degradable microspheres prepared according to the process described herein, which may be in a slurry, a powder, or a suspension. The quantity of microspheres in the kit may vary depending on the specific intended application. The quantity of microspheres will depend on factors such as the diameter of the site to be occluded and the pressure that the occlusion must withstand. Particularly useful is a kit containing swellable and degradable microspheres, prepared according to the process described herein, in a suspension, and optionally at least one syringe and/or catheter delivery device for use in administering the microspheres. The kit may also include a biocompatible carrier. Optionally included in a kit are instructions for use of the components.

EXAMPLES

The present invention is further defined in the following Examples. These Examples are given by way of illustration only, and should not be construed as limiting. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec" means second(s), "µL" means microliter(s), "mL" means milliliter(s), "L" means liter(s), "nm" means nanometer(s), "mm" means millimeter(s), "cm" means centimeter(s), "μm" means micrometer(s) or micron(s), "mM" means millimolar, "M" means molar, "g" means gram(s), "mol" means mole(s), "rpm" means revolutions per minute, "wt %" means percent by weight, "PBS" means phosphate buffered saline.

General Materials and Methods

Chemicals and other ingredients were purchased from Aldrich (Milwaukee, Wis.) and used as received, unless otherwise specified. Solvents were purchased from EMD Chemical (Darmstadt, Germany) or Aldrich, as specified below. The VA-044 polymerization initiator was used as received from Wako Pure Chemical Industries, Ltd (Richmond, Va.). All cell culture media were purchased from American Type Culture Collection (ATCC, Manassas, Va.).

Method of Measurement of Microsphere Swell

Swell ratio was determined according to a method described in the following reference: Figuly, Garret D., et. al. *Macromolecules* 1997, 30, 6174-6184. Into a pre-dried, tared, 150 mL coarse fritted funnel was added approximately 1 g of microspheres. The stem of the funnel was sealed with a rubber stopper. The funnel was placed on a filter flask, and about 150 mL of distilled water at room temperature was added to the funnel and its contents. The contents were stirred, if necessary, to fully disperse the water and microspheres. The contents were left undisturbed for 15 min. The stopper was then removed from the stem of the funnel, and suction was applied for 5 min. The stem and the underside of the funnel were then rinsed with ethanol to remove any remaining water droplets, and suction was then continued for an additional 5 min. Any remaining water droplets were wiped off of the funnel. The funnel and contents were then weighed to determine the weight of water retained by the microspheres. Swell was calculated as follows:

$$\text{swell} = \frac{[(\text{total mass of wet microshperes} + \text{funnel}) - (\text{total mass of dry microspheres} + \text{funnel})]}{\text{mass of dry microspheres}}$$

$$= \frac{[\text{wet mass of microspheres} - \text{dry mass of microspheres}]}{\text{dry mass of microspheres}}$$

$$= \text{mass water retained(g)} / \text{mass of dry microspheres(g)}$$

Method of Determining the Molecular Weight Distribution of Microsphere Degradation Products:

The molecular weight distribution of the polymer resulting from the degradation of the microspheres was determined using size exclusion chromatography with multi-angle light scattering detection (SEC-MLAS). The analysis was done with a Waters Alliance® 2690 (solvent delivery and autoinjector) system (Waters Corp., Milford, Mass.) using three columns, i.e., 2 SUPREMA M columns and 1 SUPREMA 1000 Å column, both from Polymer Standards Service (Silver Springs, Md.). The mobile phase was phosphate buffered saline, pH 7.4 (0.01 M phosphate buffer, 0.0027 M potassium chloride and 0.137 M sodium chloride) and the flow rate was 0.5 mL per minute. The eluant from the columns was directed first to a HELEOS multi-angle light scattering detector (Wyatt Technology Corp., Santa Barbara, Calif.), then to a ViscoStar™ differential viscometer (Wyatt Technology Corp.), and then finally to a Model 410 differential refractometer (Waters Corp.). The columns were housed in an oven at a temperature of 30° C. The differential refractometer was also maintained at a temperature of 30° C.

The data was acquired and analyzed using Astra software from Wyatt Technology Corp. The concentration at each elution volume was determined using the known dn/dc of 0.179, and the response of the differential refractometer. The molecular weight at each elution time was calculated from the excess light scattering intensities, not from the elution time, and was not determined relative to standards. Molecular weight averages ($M_n$, $M_w$, etc.) were calculated using the standard summation expressions, as is known in the art.

Example 1

Preparation of Swellable and Degradable Microspheres from Acrylic Acid Using No Crosslinker and Drying at 100° C.

The purpose of this Example was to prepare swellable and degradable microspheres according to the method disclosed herein. Specifically, the microspheres were prepared in absence of a crosslinking agent and were heated at a temperature of 100° C. for 2-3 days. The resulting non-crosslinked microspheres did not dissolve readily.

Into a 5 L round-bottom, three-necked flask equipped with an overhead stirrer, thermometer, reflux condenser, and nitrogen inlet port was prepared a solution of 36.0 g ethyl cellulose, 1200 mL chloroform, and 570 g methylene chloride (solution A). The mixture was stirred at 200 rpm until the ethyl cellulose dissolved; then the agitator was maintained at 200-250 rpm to create a slight vortex. In a second flask, was prepared a solution of 1.50 g methyl cellulose, 26.01 g Triton™ X-405, and 149.4 g water (solution B). In a third separate flask was mixed 58.5 g acrylic acid and 75.0 g of a 25% aqueous sodium hydroxide solution (to reach a pH of between 5 and 6) (solution C). This acrylic acid solution was then added to the water solution B.

At this point, while rapidly stirring the mix of Solutions B and C, 0.15 g of the water-soluble azo initiator VA-044 (2,2'-azobis[2-(2-imidazolin-2-yl)propane]dihydrochloride) was added and the resulting solution was stirred for 5 min to form the "first solution". The first solution was then added to the round-bottom flask containing solution A (the "second solution"). The resulting reaction mixture was stirred at 190 rpm for about 1 h at room temperature, forming the "first suspension". The first suspension was then heated to 52° C. and stirred at 140 rpm for an additional 6 h at that temperature, forming the "second suspension". The second suspension was stirred at 140 rpm for 14 h at room temperature. After that time, approximately 2000 mL of methanol was slowly added to the second suspension and the microspheres were stirred for an additional hour. The microspheres were then filtered, washed with an additional 250 mL of methanol, filtered again, and finally washed with 250 mL of ethanol. The microspheres were then dried in a nitrogen-purged vacuum oven set at 100° C. for 2 to 3 days. The resulting microspheres were white in color. The final yield of dried microspheres was 67.92 g.

The resulting dried microspheres exhibited diameters generally ranging from 15 μm to 425 μm as measured from photos acquired via scanning electron microscopy. Microsphere swell was tested as described in General Methods. When exposed to water, the microspheres absorbed 71 g of water/g of microspheres.

In an attempt to dissolve the microspheres, 0.10 g of dried microspheres was placed into a vial filled with 20 mL of distilled water and shaken on a rotary shaker for 7 days. After that time, the resulting material was removed from the vial via filtration. The resulting residual mass of microspheres recovered was 0.06 g, demonstrating that the microspheres do not readily dissolve in water even though they were prepared without a crosslinker.

Example 2

Comparative

Preparation of Swellable Microspheres from Acrylic Acid Using a Crosslinker and Drying at 100° C.

The purpose of this comparative Example was to prepare microspheres according to the method described by Figuly et al. in copending and commonly owned US Patent Application Publication No. US 2007/0237956. Specifically, the microspheres were prepared in the presence of a crosslinking agent (i.e., N,N'-methylenebisacrylamide) and were heated at a temperature of 100° C. for 2-3 days.

Into a 5 L round-bottom, three-necked flask equipped with an overhead stirrer, thermometer, reflux condenser, and nitrogen inlet port was prepared a solution of 36.0 g ethyl cellulose, 1200 mL chloroform, and 570 g methylene chloride (solution A). The mixture was stirred at 200 rpm until the ethyl cellulose dissolved; then the agitator was maintained at 200-250 rpm to create a slight vortex. In a second flask, was prepared a solution of 1.50 g methyl cellulose, 3.00 g N,N'-methylenebisacrylamide (crosslinker), 26.01 g Triton X-405, and 149.4 g water (solution B). In a third separate flask was mixed 58.5 g acrylic acid and 75.0 g of a 25% aqueous sodium hydroxide solution (to reach a pH of between 5 and 6) (solution C). This acrylic acid solution was then added to the water solution B.

At this point, while rapidly stirring the mix of Solutions B and C, 0.15 g of the water-soluble azo initiator VA-044 (2,2'-azobis[2-(2-imidazolin-2-yl)propane]dihydrochloride) was added and the resulting solution was stirred for 5 min. This solution was then added to the round-bottom flask containing solution A. The resulting reaction mixture was stirred at about 200 rpm for about 1 h at room temperature. It was then heated to 52° C., stirred at 140 rpm for an additional 6 h at that temperature, and then stirred another 14 h at room temperature. After this time, approximately 2000 mL of methanol was slowly added to the reaction mixture and the microspheres were stirred for an additional hour. The microspheres were then filtered, washed with an additional 250 mL of methanol, filtered again, and finally washed with 250 mL of ethanol. The microspheres were then dried in a nitrogen purged vacuum oven set at 100° C. for 2 to 3 days. The resulting microspheres were white in color. The final yield of dried microspheres was 72.03 g.

The resulting dried microspheres exhibited diameters generally ranging from 30 μm to 265 μm as measured from photos acquired via scanning electron microscopy. Microsphere swell was tested as described in General Methods. When exposed to water, the microspheres absorbed 109 g of water/g of microspheres. The diameter of a dry microsphere was measured to be 105.5 μm and the wet diameter of the same microsphere was measured to be 590.2 μm, yielding a wet diameter/dry diameter ratio of 5.59.

Examples 3 and 4

Degradation Rates of Microspheres Prepared with and without Crosslinker

The purpose of these Examples was to compare the degradation rates of microspheres prepared without a crosslinker (Example 1) with microspheres prepared with a crosslinker (Comparative Example 2).

Into one 4 ounce (118 mL), wide-mouth jar was placed 0.5 g of the crosslinked microspheres produced in Comparative Example 2 and 50 mL of 0.1 M sodium phosphate/0.1 M sodium chloride (phosphate buffered saline—PBS) solution. Into a second identical jar was placed 0.5 g of non-crosslinked polymeric microspheres produced in Example 1 and 50 mL of 0.1 M sodium phosphate/0.1 M sodium chloride (phosphate buffered saline—PBS) solution. After 15 min of soaking at room temperature for each sample, the microspheres were vacuum filtered for 5 min and weighed to obtain an initial swell weight. The resulting swollen microspheres were then returned to 50 mL of fresh PBS and agitated in a shaker oven set at 37° C. and 20 rpm. The samples were then filtered and weighed at pre-determined intervals to determine weight loss or gain. After weighing, the samples were returned to a fresh 50 mL portion of PBS and returned to the shaker oven set at 37° C. and 20 rpm. The results are given in Table 1.

TABLE 1

Degradation of Crosslinked and Non-Crosslinked Microspheres

| Exposure Time (h) | Example 3 - Weight of Microspheres from Example 1 (g) | Comparative Example 4 - Weight of Microspheres from Comparative Example 2 (g) |
|---|---|---|
| 0 - Initial Swell | 9.81 | 11.91 |
| 24 | 12.26 | 13.86 |
| 48 | 18.36 | 14.35 |
| 216 | 0.14 | 14.97 |
| 384 | No Sample Remained | 15.41 |
| 552 | na | 15.34 |

*na means "not applicable"

These results clearly indicate that the non-crosslinked microspheres maintained a swollen structure for at least 48 h and completely degraded after 16 days (384 h) at these conditions. In contrast, the crosslinked microspheres did not degrade after 23 days (552 h) at the same conditions.

The molecular weight distribution of the polymer resulting from the degraded microspheres of Example 3 was determined using size exclusion chromatography, as described in General Methods. The number average molecular weight was $M_n$=964,000, and the weight-average molecular weight was $M_w$=1,093,000.

Example 5

Cytotoxicity Testing of the Degradation Products from Degradable Poly(Acrylic Acid) Microspheres The purpose of this Example was to demonstrate the non-cytotoxicity of the degradation products of the degradable microspheres prepared in Example 1.

Degradable poly(acrylic acid) microspheres (microspheres from Example 1) were completely degraded in phosphate buffered saline (PBS), as described in Example 3, at a concentration of 10 mg/mL prior to the cytotoxicity measurements. A dose response cytotoxicity test was conducted with NIH3T3 human fibroblast cell cultures to determine the cytotoxicity threshold of the dissolved poly(acrylic acid). The NIH3T3 human fibroblast cells were obtained from the American Type Culture Collection (ATCC). The NIH3T3 fibroblast cells were seeded at 7500 cells per well in a 96-well plate in Dulbecco's Modified Eagles Medium (DMEM) with 10% calf bovine serum (CBS). They were cultured overnight prior to replacing the medium with fresh DMEM with 10% CBS dosed with different concentrations of sterile-filtered microsphere degradation product in PBS. Cells were challenged with the dosed medium for 20 h prior to replacement with fresh medium containing 10% Alamar Blue for 3 h. The plate was read spectrophotometrically at 570 nm and 600 nm and the Alamar Blue reduction fraction was calculated as a measure of cell viability. The results summarized in Table 2 are the average and standard deviation of 4 wells per condition and are normalized to the "no treatment" control. Samples were considered to be non-cytotoxic at viabilities of 0.80 and above. The results demonstrate that the degraded poly(acrylic acid) microspheres are non-cytotoxic at concentrations up to at least 5 µg/mL.

TABLE 2

Cytotoxicity Results

| Concentration (µg/mL) | Viability - Average | Viability - Standard Deviation |
| --- | --- | --- |
| 5 | 0.947 | 0.068 |
| 2 | 1.039 | 0.045 |
| 1 | 0.990 | 0.014 |
| 0.5 | 1.058 | 0.085 |
| 0.1 | 1.052 | 0.064 |
| 0.01 | 1.041 | 0.052 |
| 0.001 | 0.930 | 0.062 |
| 0 (No Treatment) | 1.000 | 0.029 |

Example 6

Comparative

Preparation of Swellable Microspheres from Acrylic Acid Using No Crosslinker and Drying at Room Temperature The purpose of this comparative Example was to demonstrate that microspheres prepared in absence of a crosslinking agent and that are dried at room temperature dissolve readily in water.

Into a 5 L round-bottom, three-necked flask equipped with an overhead stirrer, thermometer, reflux condenser, and nitrogen inlet port was prepared a solution of 36.0 g ethyl cellulose, 1200 mL chloroform, and 570 g methylene chloride (solution A). The mixture was stirred at 200 rpm until the ethyl cellulose dissolved; then the agitator was maintained at 200-250 rpm to create a slight vortex. In a second flask, was prepared a solution of 1.50 g methyl cellulose, 26.01 g Triton X-405, and 149.4 g water (solution B). In a third separate flask was mixed 58.5 g acrylic acid and 75.0 g of a 25% aqueous sodium hydroxide solution (to reach a pH of between 5 and 6) (solution C). This acrylic acid solution was then added to the water solution B.

At this point, while rapidly stirring the mix of Solutions B and C, 0.15 g of the water-soluble azo initiator VA-044 (2,2'-azobis[2-(2-imidazolin-2-yl)propane]dihydrochloride) was added and the resulting solution was stirred for 5 min. This solution was then added to the round-bottom flask containing solution A. The reaction mixture was stirred at 200 rpm for about 1 h at room temperature. It was then heated to 52° C., stirred at 140 rpm for an additional 6 h at that temperature, and then stirred another 14 h at room temperature. After that time, approximately 2000 mL of methanol was slowly added to the reaction mixture and the microspheres were stirred for an additional hour. The microspheres were then filtered, washed with an additional 250 mL of methanol, filtered again, and finally washed with 250 mL of ethanol. The microspheres were then dried in a nitrogen-purged vacuum oven set at room temperature (i.e., about 20° C. to about 25° C.) for 2 to 3 days. The resulting microspheres were white in color. The final yield of dried microspheres was 63.9 g.

Microsphere swell was tested as described in General Methods. When exposed to water, the microspheres absorbed only 8.72 g of water/g of microspheres and formed a continuous gel, indicating that the microspheres had dissolved. No evidence of any intact microspheres was observed. After incubation of the gel at 37° C. in PBS for 24 h, no evidence of any remaining gel or microspheres was found. This result demonstrates that non-crosslinked microspheres that are not subjected to the heat-treatment step, degrade rapidly in water, unlike non-crosslinked microspheres that were heated to 100° C. for 2-3 days, as shown in Example 3.

Examples 7-17

Control of Degradation Rate of Microspheres by Using Different Drying Conditions The purpose of these Examples was to demonstrate that the degradation rate of the degradable microspheres can be controlled by varying the time and temperature of the heat treatment step in the process of making the microspheres.

Swellable and degradable microspheres were prepared as described in Example 1, except that after the final ethanol wash, the microspheres were heat treated in a nitrogen-purged vacuum oven at different conditions of time and temperature, as shown in Table 3.

The degradation rates of the microspheres were then determined using the method described in Examples 3 and 4. The time it took for the microspheres to completely degrade (i.e., the weight reached 0.00 g) is given in Table 3.

The results in Table 3 show that in general, heating for longer times results in a slower degradation rate for the degradable microspheres. Additionally, heating at higher temperatures also results in slower degradation. Microspheres that were not heat treated (i.e. dried at room temperature), degraded very quickly (Example 17, Comparative). These results demonstrate that the degradation rate of the degradable microspheres disclosed herein can be controlled by adjusting the temperature and time of heat treatment.

TABLE 3

Degradation of Microspheres Prepared using Different Heat Treatment Conditions

| EXAMPLE | Temperature of Heat Treatment (° C.) | Time of Heat Treatment (Days) | Time to Completely Degrade (Days) |
| --- | --- | --- | --- |
| 7 | 50 | 1 | 1 |
| 8 | 50 | 4 | 2 |
| 9 | 50 | 7 | 3 |
| 10 | 50 | 11 | 3 |

TABLE 3-continued

Degradation of Microspheres Prepared using Different Heat Treatment Conditions

| EXAMPLE | Temperature of Heat Treatment (° C.) | Time of Heat Treatment (Days) | Time to Completely Degrade (Days) |
|---|---|---|---|
| 11 | 100 | 1 | 4 |
| 12 | 100 | 4 | 7 |
| 13 | 100 | 7 | 10 |
| 14 | 100 | 11 | 7 |
| 15 | 150 | 1 | 10 |
| 16 | 150 | 4 | 7 |
| 17, Comparative | room temperature | 2 | less than 20 minutes |

What is claimed is:

1. A swellable and degradable, heat-dried microsphere preparation comprising microspheres which comprise polymer chains, said polymer chains consisting of at least one monomer selected from the group consisting of acrylic acid, methacrylic acid, salts of acrylic acid and methacrylic acid, acrylamide, methacrylamide, N-substituted acrylamides, N-substituted methacrylamides, 2-hydroxyethyl acrylate, and 2-hydroxyethyl methacrylate, provided that:
if said monomer is acrylamide, methacrylamide, N-substituted acrylamides, 2-hydroxyethyl acrylate, or 2-hydroxyethyl methacrylate, then said monomer is present in combination with at least one other monomer selected from subgroup 1 consisting of: acrylic acid, methacrylic acid, and salts of acrylic acid and methacrylic acid;

wherein:
(i) said polymer chains are not crosslinked with a crosslinking agent;
(ii) said microspheres degrade substantially completely into high molecular weight soluble polymer after a time greater than 20 minutes in vitro when incubated in phosphate-buffered saline solution in a shaker oven set at 37° C. and 20 revolutions per minute;
(iii) said microspheres have a degradation rate that is dependent on the heating temperature and time used to treat the microspheres; and (iv) said microspheres are heat-dried at a temperature of at least about 50° C. for at least about 24 h.

2. The swellable and degradable microsphere preparation according to claim 1 wherein the polymer chains comprise the monomers acrylic acid and sodium acrylate.

3. The swellable and degradable microsphere preparation according to claim 1 wherein the microspheres degrade substantially completely into high molecular weight soluble polymer after a time from 1 day to 10 days in vitro when incubated in phosphate-buffered saline solution in a shaker oven set at 37° C. and 20 revolutions per minute.

4. The swellable and degradable microsphere preparation according to claim 1 wherein the microsphere preparation is made by a process comprising the steps of:
a) forming a first solution having a pH of at least 3 or about 3 comprising:
(i) water;
(ii) at least one water miscible monomer selected from the group consisting of acrylic acid, methacrylic acid, salts of acrylic acid and methacrylic acid, acrylamide, methacrylamide, N-substituted acrylamides, N-substituted methacrylamides, 2-hydroxyethyl acrylate, and 2-hydroxyethyl methacrylate,
provided that:
(A) if said monomer is acrylamide, methacrylamide, N-substituted acrylamides, 2-hydroxyethyl acrylate, or 2-hydroxyethyl methacrylate, said monomer is used in combination with at least one other monomer selected from subgroup 1 consisting of: acrylic acid, methacrylic acid, and salts of acrylic acid and methacrylic acid;
(iii) a water soluble protecting colloid;
(iv) an emulsifier; and
(v) a water soluble azo initiator having a low activation temperature;
b) forming a second solution comprising at least one substantially chlorinated hydrocarbon of less than 6 carbon units, provided that the chlorinated hydrocarbon is not a halogenated aromatic hydrocarbon, and an organic soluble protecting colloid;
c) forming a first suspension with agitation comprising the first and second solutions at a temperature below the activation temperature of the azo initiator of (a);
d) increasing the temperature of the first suspension to a temperature at which the water soluble azo initiator is activated;
e) agitating the first suspension until it forms a second suspension comprising a gelatinous precipitate suspended in an organic liquid phase, wherein microspheres are formed;
f) allowing the second suspension to cool to a temperature that is at about 30° C. or below 30° C. while agitating the second suspension;
g) washing the second suspension at least once with a dehydrating solvent wherein water is removed from the microspheres, producing a microsphere slurry comprising washed microspheres;
h) recovering the washed microspheres from the microsphere slurry; and
i) heating the washed microspheres to a temperature of at least about 50° C. for at least about 24 h for a time sufficient to substantially dry the washed microspheres to form the swellable and degradable microsphere preparation;
wherein the process is carried out in absence of a crosslinking agent.

5. The swellable and degradable microsphere preparation according to claim 4 wherein the second solution of (b) comprises a mixture of chloroform and methylene chloride.

6. The swellable and degradable microsphere preparation according to claim 4 wherein the second solution comprises a combination of methylene chloride and a solvent or solvent mixture having a sum of differences in Hansen solubility parameters relative to the Hansen solubility parameters of chloroform of less than about 0.21.

7. The swellable and degradable microsphere preparation according to claim 4 wherein the azo initiator of (a) has an activation temperature that is about 55° C. or less than 55° C.

8. The swellable and degradable microsphere preparation according to claim 7 wherein the azo initiator is 2,2'-azobis (2-[2-imidazolin-2-yl])propane dihydrochloride.

9. The swellable and degradable microsphere preparation according to claim 4 wherein the protecting colloid of (a) is a water soluble cellulose ester or ether.

10. The swellable and degradable microsphere preparation according to claim 9 wherein the protecting colloid is methyl cellulose.

11. The swellable and degradable microsphere preparation according to claim 4 wherein the protecting colloid of (b) is an organic soluble cellulose ester or ether.

12. The swellable and degradable microsphere preparation according to claim 11 wherein the protecting colloid is ethyl cellulose.

13. The swellable and degradable microsphere preparation according to claim 4 wherein the emulsifier of (a) is a non-ionic surfactant.

14. The swellable and degradable microsphere preparation according to claim 13 wherein the emulsifier is an alkylaryl polyether alcohol preparation.

15. The swellable and degradable microsphere preparation according to claim 4 wherein the first suspension of (c) is formed at a temperature of about 30° C. or below 30° C.

16. The swellable and degradable microsphere preparation according to claim 4 wherein the temperature in (d) is between about 50° C. and 55° C.

17. The swellable and degradable microsphere preparation according to claim 4 wherein the heating of step (i) is at a temperature of about 50° C. to about 150° C.

18. A method for embolization in a mammal comprising administering into the vasculature of said mammal, the swellable and degradable microsphere preparation of claim 1.

19. The method for embolization according to claim 18 wherein the microsphere preparation is prepared by a process comprising the steps of:
   a) forming a first solution having a pH of at least 3 or about 3 comprising:
      (i) water;
      (ii) at least one water miscible monomer selected from the group consisting of acrylic acid, methacrylic acid, salts of acrylic acid and methacrylic acid, acrylamide, methacrylamide, N-substituted acrylamides, N-substituted methacrylamides, 2-hydroxyethyl acrylate, and 2-hydroxyethyl methacrylate,
      provided that:
         (A) if said monomer is acrylamide, methacrylamide, N-substituted acrylamides, 2-hydroxyethyl acrylate, or 2-hydroxyethyl methacrylate, said monomer is used in combination with at least one other monomer selected from subgroup 1 consisting of: acrylic acid, methacrylic acid, and salts of acrylic acid and methacrylic acid;
      (iii) a water soluble protecting colloid;
      (iv) an emulsifier; and
      (v) a water soluble azo initiator having a low activation temperature;
   b) forming a second solution comprising at least one substantially chlorinated hydrocarbon of less than 6 carbon units, provided that the chlorinated hydrocarbon is not a halogenated aromatic hydrocarbon, and an organic soluble protecting colloid;
   c) forming a first suspension with agitation comprising the first and second solutions at a temperature below the activation temperature of the azo initiator of (a);
   d) increasing the temperature of the first suspension to a temperature at which the water soluble azo initiator is activated;
   e) agitating the first suspension until it forms a second suspension comprising a gelatinous precipitate suspended in an organic liquid phase, wherein microspheres are formed;
   f) allowing the second suspension to cool to a temperature that is at about 30° C. or below 30° C. while agitating the second suspension;
   g) washing the second suspension at least once with a dehydrating solvent wherein water is removed from the microspheres, producing a microsphere slurry comprising washed microspheres;
   h) recovering the washed microspheres from the microsphere slurry; and
   i) heating the washed microspheres to a temperature of at least about 50° C. for at least about 24 h for a time sufficient to substantially dry the washed microspheres to form the swellable and degradable microsphere preparation;
wherein the process is carried out in absence of a crosslinking agent.

* * * * *